US012788433B2

(12) United States Patent
Balkovec et al.

(10) Patent No.: US 12,788,433 B2
(45) Date of Patent: Nov. 10, 2026

(54) APPARATUS AND METHOD FOR TISSUE PUNCTURE DURING PERICARDIOCENTESIS

(71) Applicant: Boston Scientific Medical Device Limited, Galway (IE)

(72) Inventors: Christian Balkovec, Burlington (CA); Eduardo Moriyama, Richmond (CA); Gareth Davies, Toronto (CA); Matthew DiCicco, Toronto (CA)

(73) Assignee: Boston Scientific Medical Device Limited, Galway (IE)

( * ) Notice: Subject to any disclaimer, the term of this patent is extended or adjusted under 35 U.S.C. 154(b) by 455 days.

(21) Appl. No.: 18/468,202

(22) Filed: Sep. 15, 2023

(65) Prior Publication Data

US 2024/0090919 A1 Mar. 21, 2024

Related U.S. Application Data

(60) Provisional application No. 63/375,706, filed on Sep. 15, 2022.

(51) Int. Cl.
*A61B 17/34* (2006.01)
*A61B 17/00* (2006.01)
(Continued)

(52) U.S. Cl.
CPC .......... *A61B 17/3417* (2013.01); *A61B 90/39* (2016.02); *A61M 39/10* (2013.01);
(Continued)

(58) Field of Classification Search
CPC .................. A61M 25/01; A61M 25/09; A61M 25/09041; A61M 2025/09058;
(Continued)

(56) References Cited

U.S. PATENT DOCUMENTS 5,964,754 A 10/1999 Osypka
9,717,523 B2 8/2017 Feng et al.
(Continued)

FOREIGN PATENT DOCUMENTS

CN 104546074 A 4/2015
JP 2008-512212 A 4/2008
(Continued)

OTHER PUBLICATIONS

International Search Report and Written Opinion received for PCT Patent Application No. PCT/EP2023/075446, mailed on Nov. 23, 2023, 7 pages.

(Continued)

*Primary Examiner* — Jocelin C Tanner
(74) *Attorney, Agent, or Firm* — Nelson Mullins Riley & Scarborough LLP

(57) ABSTRACT

A method and apparatus are disclosed for an elongated introducer assembly and an elongated guidewire assembly. The elongated introducer assembly is manipulated and positioned proximate to a first biological wall. An elongated guidewire assembly is selectively maneuvered along the elongated introducer assembly and is comprised of a distal tip, distal portion, and elongated shaft section. The distal portion is further comprised of a flexible preset spatial geometry which comprises a distal length and distal deflective portion. The distal tip is used to puncture the first biological wall and the distal deflective portion directs the distal length away from a second biological wall positioned proximate to the first biological wall.

13 Claims, 15 Drawing Sheets

(51) Int. Cl.

| | |
|---|---|
| ***A61B 90/00*** | (2016.01) |
| ***A61M 39/10*** | (2006.01) |
| ***A61M 39/22*** | (2006.01) |

(52) U.S. Cl.
CPC ... *A61M 39/22* (2013.01); *A61B 2017/00243* (2013.01); *A61B 2017/00336* (2013.01); *A61B 2017/00867* (2013.01); *A61B 2017/3454* (2013.01); *A61B 2090/3925* (2016.02)

(58) Field of Classification Search
CPC ........... A61M 2025/09141; A61M 2025/0915; A61M 2025/09125; A61M 2025/09116; A61M 2025/09175; A61M 39/10; A61M 39/22; A61B 17/00; A61B 17/22; A61B 17/3417; A61B 17/3478; A61B 90/39; A61B 2017/00243; A61B 2017/00336; A61B 2017/00331; A61B 2017/00867; A61B 2017/22044; A61B 2017/3454; A61B 2090/08021; A61B 2090/3925
USPC ........................................................... 606/185
See application file for complete search history.

(56) References Cited

U.S. PATENT DOCUMENTS

| | | | | |
|---|---|---|---|---|
| 2005/0065507 A1* | 3/2005 | Hartley | A61B 18/1492 | 606/41 |
| 2005/0101984 A1* | 5/2005 | Chanduszko | A61B 17/0057 | 606/185 |
| 2005/0136385 A1* | 6/2005 | Mann | A61N 1/025 | 434/320 |
| 2006/0009737 A1* | 1/2006 | Whiting | A61M 25/0084 | 606/167 |
| 2006/0135962 A1* | 6/2006 | Kick | A61M 25/0662 | 606/191 |
| 2009/0105654 A1* | 4/2009 | Kurth | A61M 25/09041 | 604/170.03 |
| 2012/0095434 A1* | 4/2012 | Fung | A61B 17/3478 | 604/528 |
| 2014/0094836 A1* | 4/2014 | Feng | A61B 17/3403 | 606/185 |
| 2016/0100860 A1* | 4/2016 | Lenker | A61B 17/3478 | 604/95.01 |
| 2020/0060710 A1* | 2/2020 | Urbanski | A61M 29/00 | |
| 2020/0114128 A1* | 4/2020 | Roeder | A61M 25/09 | |
| 2021/0228268 A1 | 7/2021 | Urbanski et al. | | |

FOREIGN PATENT DOCUMENTS

| | | |
|---|---|---|
| JP | 2021-522905 A | 9/2021 |
| WO | 2011/043126 A1 | 4/2011 |
| WO | 2021/255553 A1 | 12/2021 |

OTHER PUBLICATIONS

Notice of Reasons for Refusal received for Japanese Patent Application No. 2025-515717, mailed on Feb. 10, 2026, 14 pages (7 pages of English Translation and 7 pages of Original Document).

* cited by examiner

APPARATUS AND METHOD FOR TISSUE PUNCTURE DURING PERICARDIOCENTESIS

CROSS REFERENCE TO RELATED APPLICATIONS

This application claims the benefit of priority to U.S. Provisional Application Ser. No. 63/375,706, titled “APPARATUS AND METHOD FOR TISSUE PUNCTURE DURING PERICARDIOCENTESIS,” filed Sep. 15, 2022, the entire disclosure of which is incorporated herein by reference in its entirety.

TECHNICAL FIELD

The disclosure relates to the apparatus and methods for puncture of a biological wall. More specifically, the apparatus is configured for puncturing the pericardium of the heart.

SUMMARY

Pericardiocentesis is a procedure performed when there is an excessive buildup of fluid within the space between the pericardial sac and the myocardium of the heart, necessitating drainage of the fluid from the space. Performing a pericardiocentesis procedure involves puncturing the pericardium, which surrounds the myocardium of the heart (without puncturing the myocardium). It is known that mechanical needles may be used to puncture the pericardium layer, where the user must exercise great care to control the input force of the needle to puncture the pericardium while avoiding, as best as possible, damaging the underlying myocardium.

Known pericardium puncture devices and methods also include use of puncture guidewires with a sharp distal tip to create a puncture hole. The known puncture guidewires, unfortunately, have a pre-set distal curve shape where the sharp distal tip rapidly deflects away from the desired puncture direction to avoid inadvertent puncture, or damage to the myocardium directly adjacent the pericardium. The rapidly deflecting sharp distal tip may prevent puncture of the pericardium in instances where there is a layer of fat covering the pericardium, or where a patient has a thickened pericardium, as the puncture wire protrudes from the lumen of a hollow needle and may begin to deviate before it has punctured through the full thickness of the pericardium layer. In pericardiocentesis procedures, the buildup of fluid positions the pericardium further away from the myocardium than is typical, and thus, a puncture wire for this application does not need a distal curve shape that deflects at such a short distance from the distal tip.

Known pericardium puncture methods also include use of radiofrequency (RF) puncture devices such as needles or guidewires that use RF energy activated for a fraction of a second to selectively vaporize tissue via a blunt electrode. Use of these RF devices requires setup of cables, generators, and other electrical apparatus that may require more time than is preferred to perform a pericardiocentesis procedure under circumstances where the buildup of fluid is an emergency and the need to drain the fluid is immediate. Therefore, there is a need for an apparatus and method for puncturing of a first biological wall while avoiding inadvertent puncture of a second biological wall or myocardium, and while reducing device exchanges, complexity, and time.

SUMMARY OF THE DISCLOSURE

In one broad aspect of the present disclosure, an apparatus is provided which comprises a synergistic combination of an elongated introducer assembly and an elongated guidewire assembly. The elongated introducer assembly is configured to be positioned proximate to a first biological wall and slidably receive the elongated guidewire assembly. The elongated guidewire assembly has a distal portion with a flexible preset spatial geometry that may be selectively maneuvered along the elongated introducer assembly. A distal tip on the elongated guidewire assembly is used to puncture the first biological wall and a distal deflective portion directs a distal length away from the leading edge of the elongated guidewire assembly when maneuvered out of the elongated introducer apparatus.

According to one aspect of the present disclosure, an apparatus for engaging and puncturing a tissue of a patient having a first biological wall and a second biological wall proximate to said first biological wall is provided. The apparatus comprises an elongated introducer assembly configured to be maneuvered toward and positioned proximate to the first biological wall of the patient. The elongated introducer assembly is configured to slidably receive an elongated guidewire assembly, and the elongated guidewire assembly has a distal portion with a flexible pre-set spatial geometry configured to be selectively maneuvered along the elongated introducer assembly. The elongated guidewire assembly has a distal tip that is configured to form, at least in part, a puncture hole extending through said first biological wall; and the distal portion adopts a straightened state when inside the elongated introducer assembly and adopts a pre-set spatial geometry when maneuvered out of said elongated introducer assembly. The pre-set spatial geometry has a distal deflective portion that begins at minimum length range of 4 mm from said distal tip and deflects a distal length away from the second biological wall. In an embodiment, the distal portion is comprised of an elastic material such as nitinol or stainless steel. The distal tip is configured to pierce the first biological wall to form, at least in part, the puncture hole. The distal portion is, for example, in a flattened configuration with a height between 0.003" and 0.005".

In an embodiment, the elongated introducer assembly further comprises a stylet configured to be slidably received by the elongated introducer assembly to provide enhanced stiffness to guide the elongated introducer assembly through the tissues surrounding the abdominal and thoracic cavities and position the introducer proximate to the pericardium. In another embodiment, the distal section of the elongated introducer assembly may incorporate an ultrasonically visible marker which is configured to be detectable by a medical imaging system. In an embodiment, the ultrasonically visible marker may be made of platinum, tungsten, gold, or any material that attenuates sound waves used with the medical imaging system.

In another embodiment, the distal length of the elongated guidewire assembly comprises a first distal length section and a second distal length section, whereby the second distal length section contains the distal tip and is deflected from the first distal length section and generally opposite the distal deflective portion. The width of the distal tip can be, for example, equal or less than 0.001".

In another embodiment, the elongated guidewire assembly has a detectable marker, configured to be detectable by a medical imaging system. In another embodiment, the detectable marker comprises a metal coil positioned over an elongated shaft section or the distal portion. In a particular embodiment, the detectable marker may be comprised of grooves, etchings, cuts, or roughened regions on the elongated shaft section or the distal portion.

As another feature, the elongated introducer assembly has a proximal hub comprising a female center luer connector and a hemostasis valve.

In another broad aspect, the disclosure provides a device and method for engaging a tissue of a patient having a first biological wall and a second biological wall proximate to the first biological wall. In an embodiment, an elongated guidewire assembly with a distal portion that has a flexible pre-set spatial geometry is slidably received by the elongated introducer assembly and maneuvered towards the first biological wall through the introducer. A distal tip at the end of a distal length on the elongated guidewire assembly is used to puncture the first biological wall and a distal deflective portion directs the distal length away from the leading edge of the elongated guidewire assembly as the distal portion relaxes and returns to its pre-set spatial geometry upon exit from the elongated introducer assembly.

In a further embodiment, the device (or apparatus) and method include introducing into a first biological wall and positioning an elongated introducer assembly that includes a lumen longitudinally disposed therethrough and slidably inserting an elongated guidewire apparatus having a distal portion, a distal deflective portion, a distal length and a distal tip into the hollow lumen. The distal portion is then advanced towards the first biological wall for creating a puncture hole in the first biological wall and crossing with the distal tip. The distal length is then defected away from said second biological wall via a distal deflective portion which is positioned a minimum of 4 mm away from the distal tip. The elongated introducer assembly is then removed from the patient while the elongated guidewire apparatus remains in position traversing said first biological wall through the puncture hole. After removing the elongated introducer assembly, an elongated catheter apparatus having a distal exit portal is slidably advanced over the elongated guidewire apparatus, via a distal exit portal, and across the first biological wall.

In yet another aspect, the method includes advancing into a first biological wall an elongated introducer assembly that includes a lumen longitudinally disposed therethrough and slidably inserting a stylet that is slidably received by the hollow lumen of the elongated introducer assembly. In an embodiment, the stylet is removed from the elongated introducer assembly following advancement of the elongated introducer assembly towards the first biological wall of the patient and positioning the introducer assembly proximate to the first biological wall.

In another embodiment, the elongated introducer assembly has a proximal hub comprising a hemostasis valve for injecting a fluid or aspiration at any step of the method.

Example 1 is an apparatus for engaging a tissue of a patient comprising a first biological wall and a second biological wall, wherein the second biological wall is positioned proximate to the first biological wall of the patient. The apparatus includes an elongated introducer assembly configured to be maneuvered toward and positioned proximate to the first biological wall of the patient. The elongated introducer assembly is configured to slidably receive an elongated guidewire assembly. The elongated guidewire assembly has a distal portion with a flexible preset spatial geometry configured to be selectively maneuvered along the elongated introducer assembly. The distal portion adopts a straightened state when inside the elongated introducer assembly and adopts a preset spatial geometry when maneuvered out of the elongated introducer assembly. The elongated guidewire assembly includes an elongated shaft section and a distal tip. The distal tip is configured to form, at least in part, a puncture hole extending through the first biological wall. The preset spatial geometry has a distal deflective portion that begins a minimum length range of 4 mm from the distal tip and deflects a distal length away from the second biological wall.

Example 2 is the apparatus of Example 1, wherein the elongated introducer assembly comprises a stylet configured to be slidably received by the elongated introducer assembly.

Example 3 is the apparatus of Example 1, wherein the distal portion comprises an elastic material selected from nitinol and stainless steel.

Example 4 is the apparatus of Example 1, wherein the distal tip is configured to pierce the first biological wall to form, at least in part, the puncture hole.

Example 5 is the apparatus of Example 4, wherein the distal portion is in a flattened configuration with a height between 0.003 inches and 0.005 inches.

Example 6 is the apparatus of Example 4, wherein the distal length comprises a first distal length section and a second distal length section. The second distal length section contains the distal tip and is deflected from the first distal length section and generally opposite the distal deflective portion.

Example 7 is the apparatus of Example 4, wherein the distal tip has a width no greater than 0.001 inch.

Example 8 is the apparatus of Example 1, wherein the elongated guidewire assembly includes a detectable marker configured to be detectable by a medical imaging system.

Example 9 is the apparatus of Example 8, wherein the detectable marker further comprises a metal coil positioned over the elongated shaft section or the distal portion.

Example 10. The apparatus of Example 8, wherein the detectable marker comprises grooves, etchings, cuts, or roughened regions in the elongated shaft section or the distal portion.

Example 11 is the apparatus of Example 1, wherein the elongated introducer assembly has a proximal hub.

Example 12 is the apparatus of Example 11, wherein the proximal hub further comprises a female luer connector.

Example 13 is the apparatus of Example 12, wherein the proximal hub further comprises a hemostasis valve.

Example 14 is the apparatus of Example 1, wherein an ultrasonically visible marker is positioned at a distal section of the elongated introducer assembly whereby the ultrasonically visible marker is configured to be detectable by a medical imaging system.

Example 15 is the apparatus of Example 14, wherein the ultrasonically visible marker comprises platinum, tungsten, or gold.

Example 16 is a method for engaging a tissue of a patient having a first biological wall and a second biological wall. The method includes advancing an elongated introducer assembly towards the first biological wall within the patient and positioning the elongated introducer assembly proximate to the first biological wall. The method includes slidably inserting an elongated guidewire assembly into a hollow lumen of the elongated introducer assembly and urging a distal portion of the elongated guidewire assembly the towards the first biological wall. The method includes creating a puncture hole in the first biological wall with a distal tip located on the elongated guidewire assembly. The method includes deflecting a distal length that comprises the distal tip away from the second biological wall via a distal deflective portion positioned a minimum of 4 mm away from the distal tip.

Example 17 is the method of Example 16, wherein the puncture hole is expanded by the elongated introducer assembly.

Example 18 is the method of Example 16, wherein the elongated introducer assembly is removed from the patient while the elongated guidewire assembly remains in position traversing the first biological wall through the puncture hole, and wherein an elongated catheter apparatus slidably receives the elongated guidewire assembly via a distal exit portal of the elongated catheter apparatus. The elongated guidewire assembly is used to guide the elongated catheter apparatus into the patient and across the first biological wall.

Example 19 is the method of Example 16, wherein the elongated introducer assembly further comprises a stylet that is slidably received by the hollow lumen of the elongated introducer assembly.

Example 20 is the method of Example 16, wherein a hemostasis valve is attached to a proximal hub of the elongated introducer assembly and fluid is injected or aspirated at any step.

BRIEF DESCRIPTION OF THE DRAWINGS

In order that the invention may be readily understood, embodiments of the invention are illustrated by way of examples in the accompanying drawings, in which.

DETAILED DESCRIPTION

Figure 1:
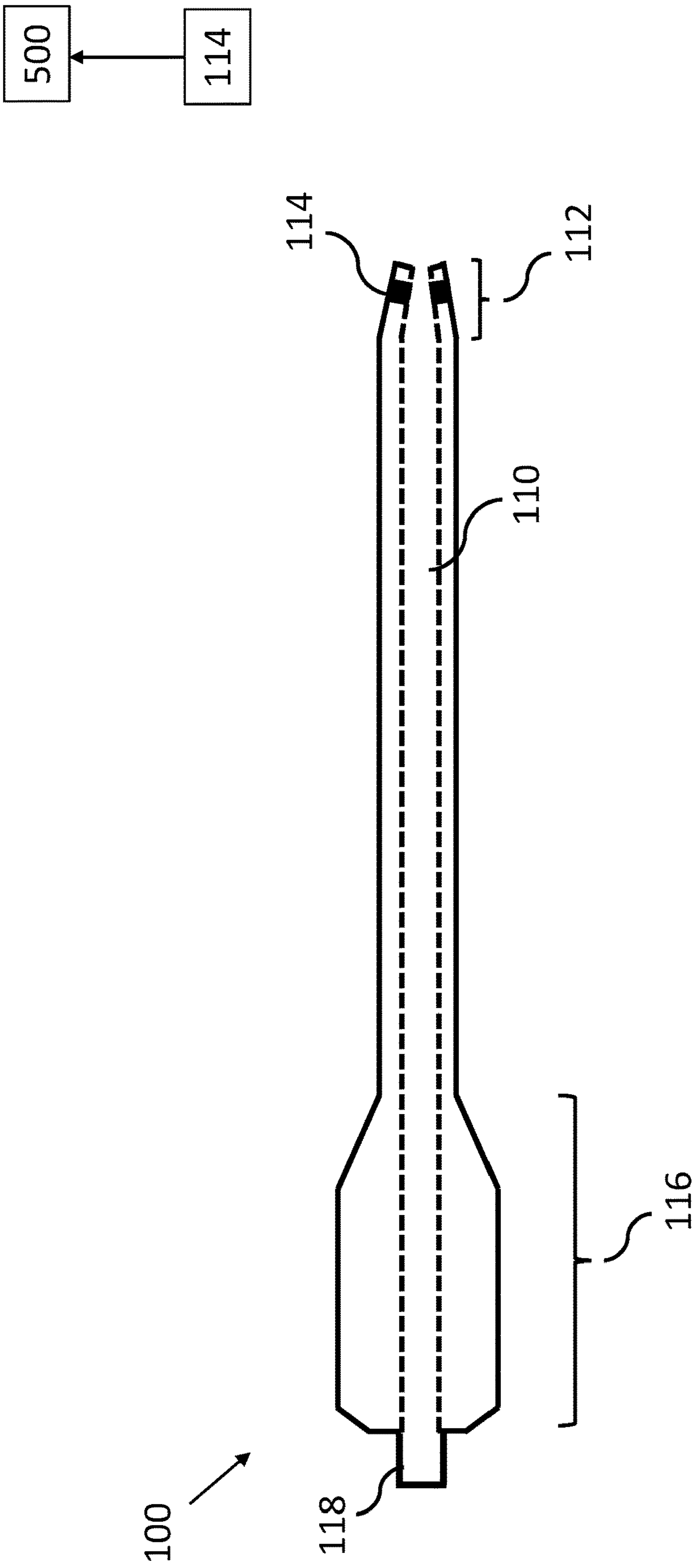
FIG. 1 depicts a cross section view of an elongated introducer assembly.

With specific reference now to the drawings in detail, it is stressed that the particulars shown are by way of example and for purposes of illustrative discussion of certain embodiments of the present invention only. Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

As further described hereinbelow, the present invention provides an apparatus and method for puncture of a first biological wall positioned proximate to a second biological wall. An elongated introducer assembly is used synergistically with an elongated guidewire assembly to puncture a first biological wall and avoid, at least in part, damage to a second biological wall.

With reference to FIG. 1, an elongated introducer assembly 100 is configured with a hollow lumen 110. The outer diameter of the elongated introducer assembly 100 may be any size that is suitable to be inserted through tissue surrounding the thoracic and abdominal cavities as well as the pericardium of the heart. The hollow lumen 110 diameter may be any size that accommodates desired accessory devices. The overall length of the elongated introducer assembly 100 may be any length that facilitates insertion through an incision below the xiphoid process to the apex of the heart. However, the elongated introducer assembly 100 may not be too long as to bend or buckle substantially under its own weight when being used. The flexural rigidity of the elongated introducer assembly 100 may be at least 0.002 $N \cdot m^2$. The elongated introducer assembly 100 may be made of any biocompatible material such as stainless steel, HDPE, LDPE, or any combination thereof. A distal section 112 of the introducer assembly 100 tapers down from the main shaft outer diameter and enhances the ability of the elongated introducer assembly 100 to advance through tissues of the body. In some embodiments, the distal section 112 may incorporate an ultrasonically visible marker 114 configured to be detectable by a medical imaging system 500. The ultrasonically visible marker may be made of platinum, tungsten, gold, or any material that attenuates sound waves used with the medical imaging system 500 in such a way that the ultrasound appears visually distinct. In this way, a user can monitor the location of the distal section 112 and use the information to aid in the positioning of the elongated introducer assembly 100. In some embodiments, the elongated introducer assembly 100 includes a proximal hub 116 that may be used for gripping or insertion of accessory devices during use. The proximal hub 116 may incorporate a female center luer connector 118 facilitating connection of luer-compatible accessories to the elongated introducer assembly 100.

Figure 2:
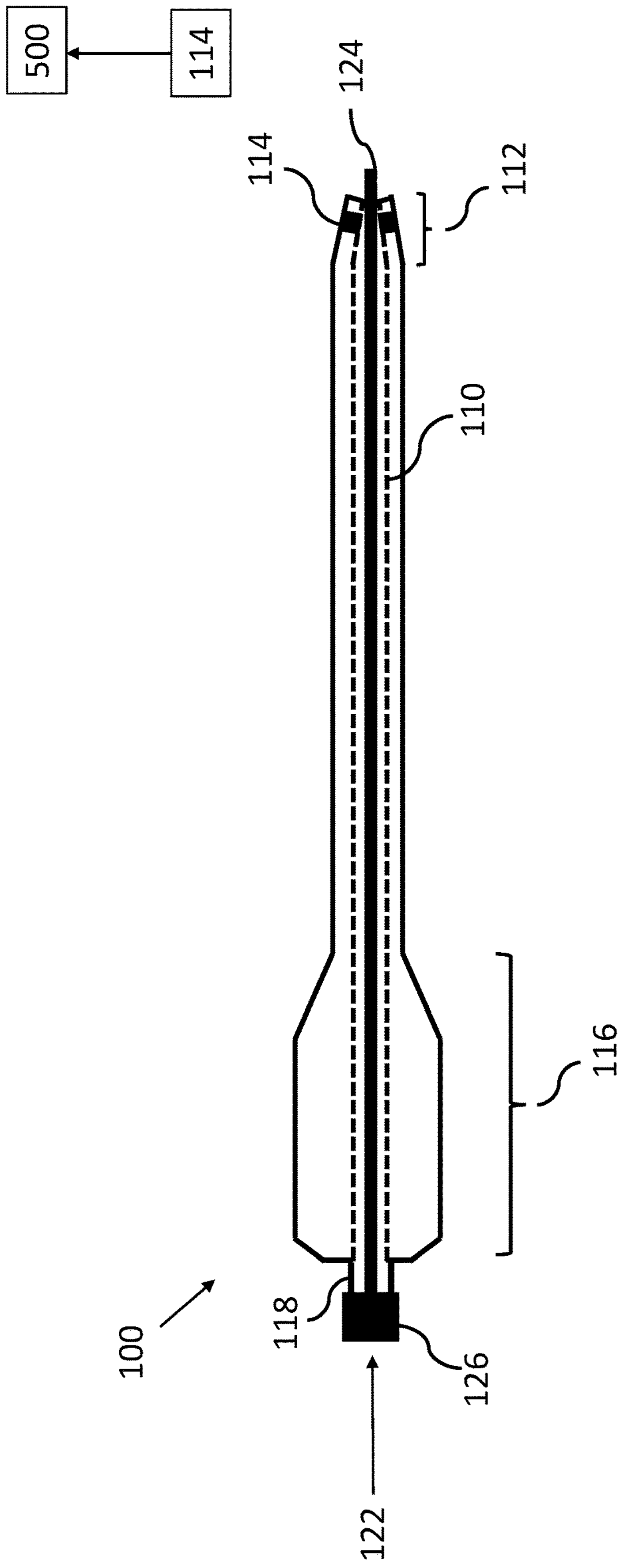
FIG. 2 depicts a cross section view of an elongated introducer assembly that includes a stylet.

With reference to FIG. 2, the elongated introducer assembly 100 is shown with the stylet 122 inside of the hollow lumen 110. The stylet 122 is comprised of a stylet shaft 124 and a stylet hub 126. The stylet 122 is fully removable from the hollow lumen 110 and may be used to add further stiffness to the elongated introducer assembly 100 during insertion and positioning while in use. In addition, the stylet 122 may also prevent the hollow lumen 110 from receiving tissue during insertion through the thorax and/or abdomen. In other words, the use or the presence of the stylet helps to mitigate extraneous tissue matter that may be embedded in the cavity of the hollow lumen 110 during insertion and positioning of the elongated introducer assembly 100 that may be deposited in the pericardium space following puncture. This extraneous tissue matter in the pericardium space may cause irritation and inflammation if deposited. Thus, occupation of the hollow lumen 110 space during insertion and positioning of the elongated introducer assembly 100 by the stylet 122 may be advantageous in that extraneous tissue matter is prevented from occupying the hollow lumen 110. The stylet shaft 124 may have an outer diameter that allows the stylet to be slidably received inside the hollow lumen 110. The stylet shaft 124 may be composed of a stiff material such as stainless steel and have a length that allows the stylet to protrude no more than 3 mm from the tip of the distal section 112 of the elongated introducer assembly 100. The stylet hub 126 may be made of any material that allows it to be gripped and manipulated. The stylet hub may enable the stylet to be fastened temporarily to the female center luer connector 118 or any other location on the proximal hub 116.

Figure 3:
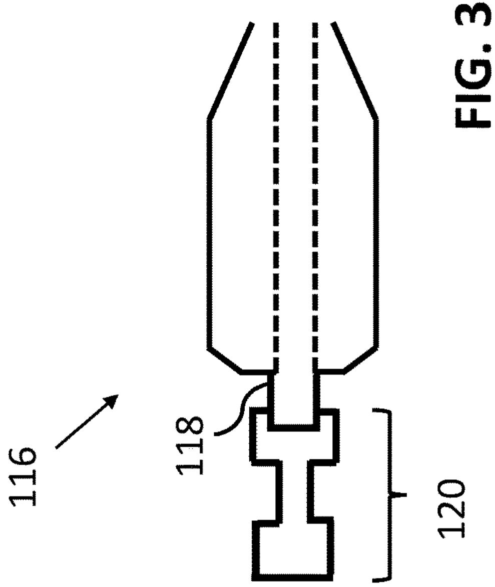
FIG. 3 depicts a cross section view of a proximal hub depicted in FIG. 1 having a hemostasis valve.

With reference to FIG. 3, the proximal hub 116 is shown with a detachable hemostasis valve 120 attached to a female center luer connector 118. The hemostasis valve 120 prevents leakage or flow of fluids while also allowing insertion and manipulation of accessory devices.

Figure 4:
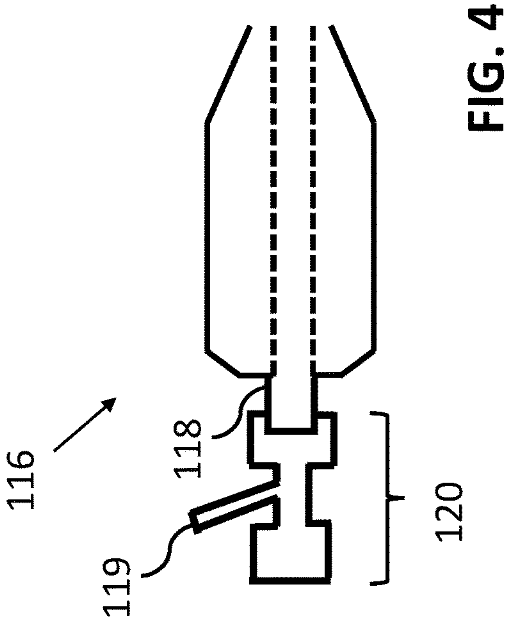
FIG. 4 depicts a cross section view of a proximal hub depicted in FIG. 1 having a hemostasis valve with a female lateral luer connector.

With reference to FIG. 4, the proximal hub 116 is shown with a detachable hemostasis valve 120 attached to a female center luer connector 118 that is integrated into the proximal hub. A female lateral luer connector 119 is shown integrated on the hemostasis valve 120 and allows for the connection of luer-compatible accessory devices while also providing an additional port to facilitate insertion and manipulation of accessory devices.

Figure 5:
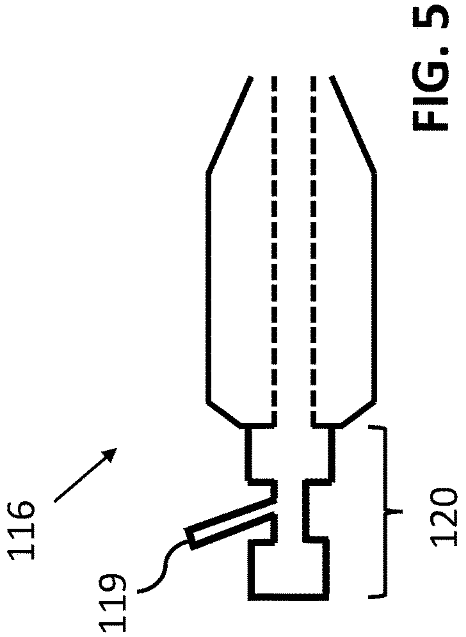
FIG. 5 cross section view of a proximal hub depicted in FIG. 1 having an alternative configuration of hemostasis valve.

With reference to FIG. 5, a proximal hub 116 is shown with a hemostasis valve 120 permanently integrated (non detachable) into the proximal hub 116. A female lateral luer connector 119 is shown on the hemostasis valve to facilitate connection of luer-compatible accessory devices while also providing an additional port to facilitate insertion and manipulation of accessory devices.

Figure 6:
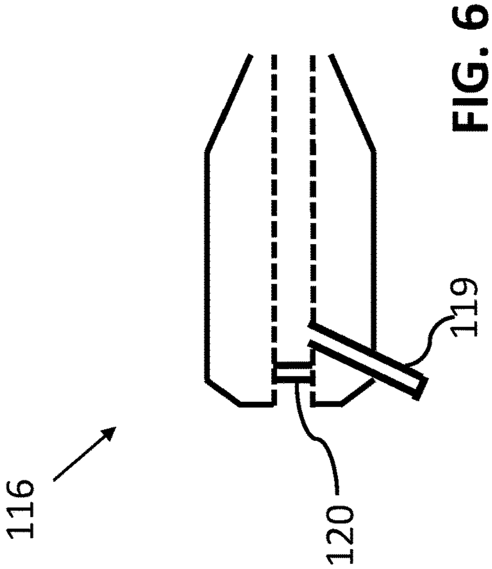
FIG. 6 depicts a cross-section view of a proximal hub depicted in FIG. 1 with a hemostasis valve inside the lumen.

With reference to FIG. 6, a proximal hub 116 is shown with a permanently integrated (non detachable) hemostasis valve 120 that prevents the backflow of fluids from the proximal hub while also allowing insertion and manipulation of accessory devices. A female lateral luer connector 119 is shown integrated into the proximal hub, allowing the connection of luer-compatible accessory devices.

Figure 7:
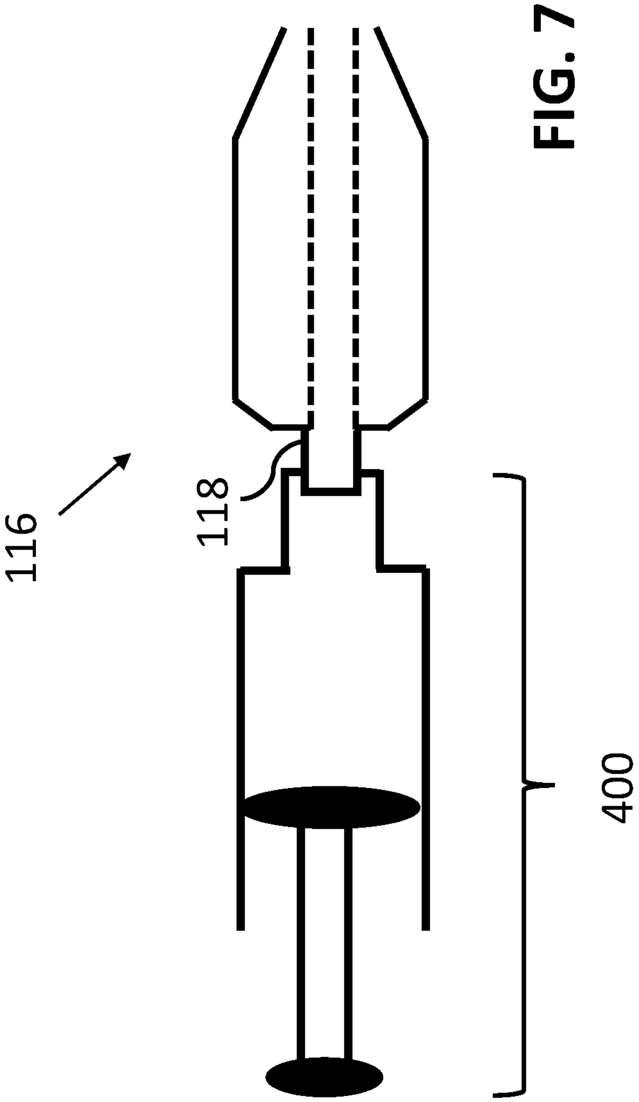
FIG. 7 depicts a side view of a proximal hub and a hemostasis valve with a syringe attached.

With reference to FIG. 7, a proximal hub 116 is shown with a female center luer connector 118 and a syringe 400 attached to the female center luer connector 118. The attachment of the syringe 400 to the proximal hub 116 facilitates the injection and aspiration of fluids by a user.

Figure 8:
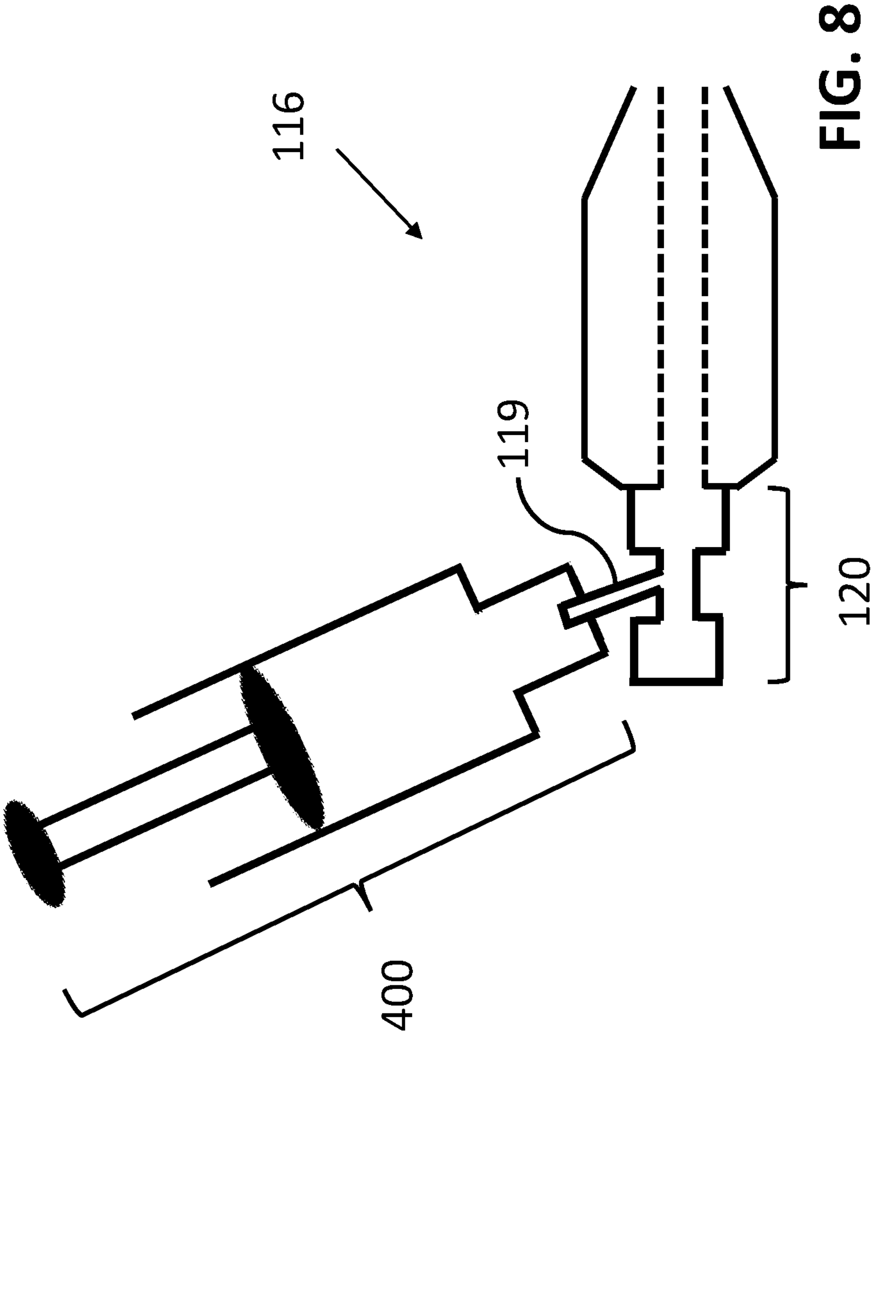
FIG. 8 depicts a side view of a proximal hub with a syringe attached.

With reference to FIG. 8, a proximal hub 116 is shown with an integrated hemostasis valve 120 and female lateral luer connector 119. A syringe 400 is attached to the female lateral luer connector 119, facilitating injection and aspiration of fluids by a user while also being able to insert and manipulate accessory devices through the hemostasis valve 120.

Figure 10:
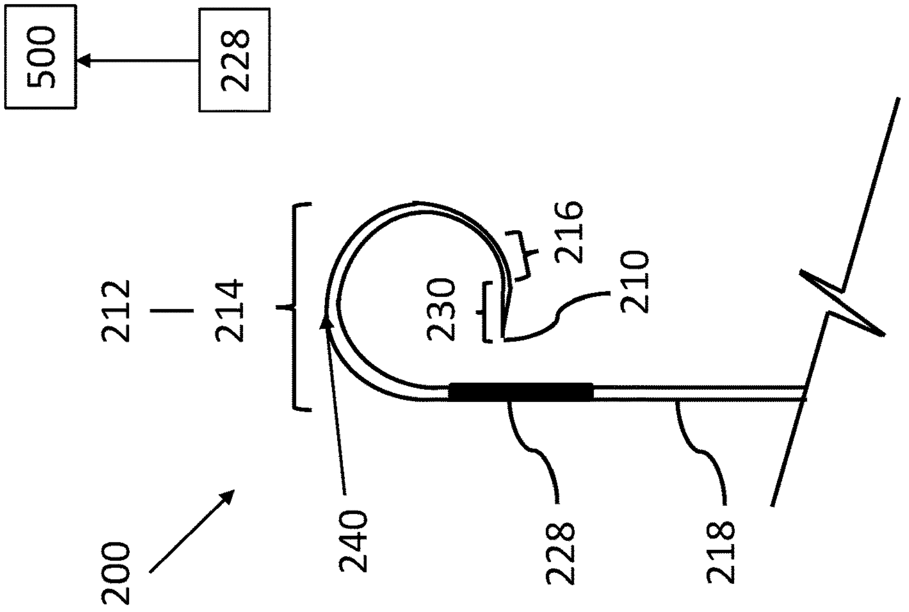
FIG. 10 depicts a side view of an elongated guidewire assembly with a curve of 270 degrees.
Figure 9:
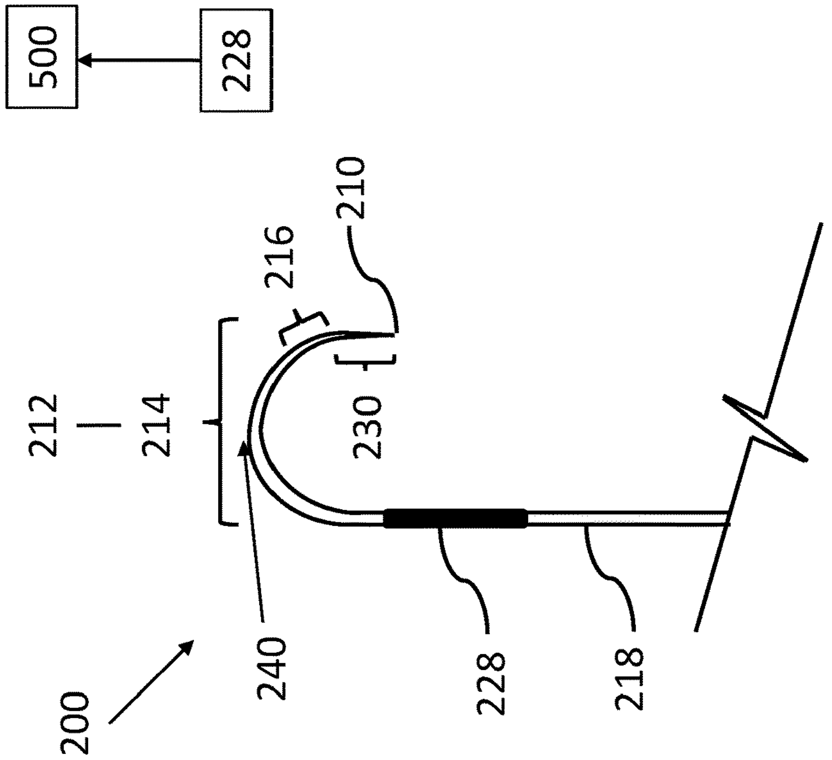
FIG. 9 depicts a side view of an elongated guidewire assembly with a curve of 180 degrees.

With reference to FIG. 9 and FIG. 10, an elongated guidewire assembly 200 is shown and comprises a distal portion 212 and an elongated shaft section 218. The distal portion 212 comprises a flexible pre-set spatial geometry 214 further comprising a distal tip 210, distal length 230, and distal deflective portion 216. The distal tip 210 may be sharp, with a width no greater than 0.001" (inches) and acts to puncture pericardium tissue. The distal deflective portion 216 is positioned no less than 4 mm back from the distal tip 210 to allow for sufficient puncture depth through thickened pericardium tissue or pericardium tissue with a thick layer of fat on top of the pericardium tissue. The distal deflective portion 216 further functions to direct the distal tip away from the trajectory that a distal length 230 takes through pericardium tissue when puncturing. When in a fully relaxed state, the distal tip 210 is fully deflected away from the leading edge 240 of the elongated guidewire assembly 200. The distal portion 212 may be comprised of a flexible material such as super-elastic nitinol. The elongated shaft section 218 may be rigid or may also be flexible and comprised of super-elastic nitinol. Typically, guidewires may vary in length between 80 cm and 450 cm and taper down from a larger cross-section to a smaller cross-section. Given this, the distal portion 212 may have a smaller diameter than the elongated shaft section 218. The diameter of the elongated shaft section may be any diameter that fits through a target accessory device (for example, the assembly 100, as well as the catheter 300). Typically, guidewires have an outer diameter ranging from 0.014" to 0.038". In some embodiments, a detectable marker 228 may be positioned on the elongated guidewire assembly 200 to facilitate visibility under a medical imaging system 500 such as ultrasound. The detectable marker 228 may be a round wire, close wound to form a coil that fits over the elongated shaft section 218 or distal portion 212. The detectable marker 228 may be made of platinum, tungsten, gold, or any material that attenuates ultrasound waves in a differential manner than that of the material comprising the distal portion 212 or the elongated shaft section 218. Additionally, the detectable marker 228 may be surface structures comprised of grooves, etchings, cuts, or roughened regions in the material of the elongated guidewire assembly 200 where such surface structures sufficiently attenuate ultrasound waves to appear visually distinct on a medical imaging system 500. In this way, the detectable marker 228 may aid a user in monitoring the position of the elongated guidewire assembly during puncture and positioning.

Figure 11:
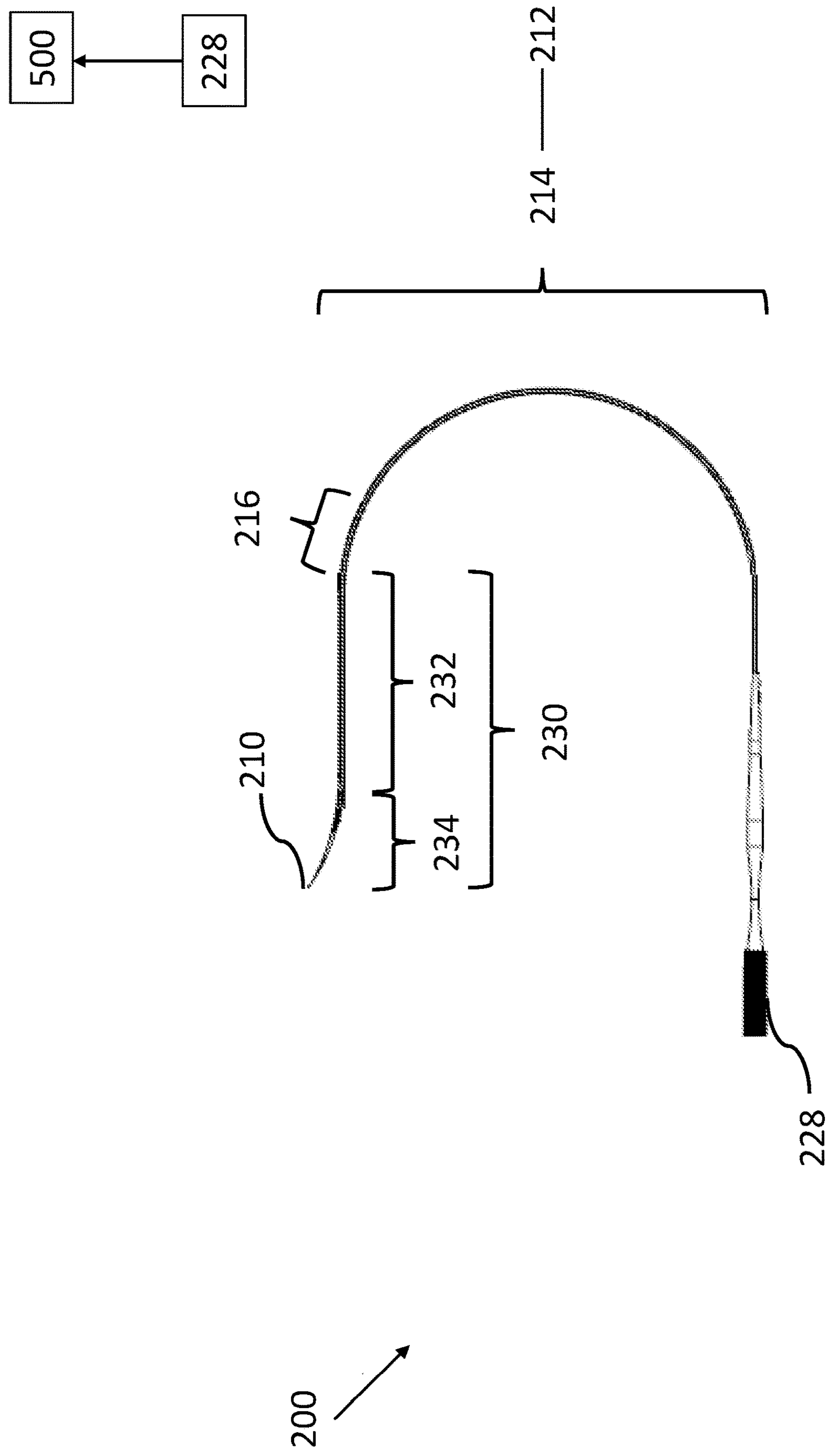
FIG. 11 depicts a side view of an elongated guidewire assembly with a slightly curved distal tip 210.

With reference to FIG. 11, the elongated guidewire assembly 200 is shown with particular emphasis on the distal portion 212. The distal portion 212 comprises a flexible pre-set spatial geometry 214 having a distal tip 210, a distal deflective portion 216, and a distal length 230. In some embodiments the distal portion 212 may have a flattened configuration whereby the shaft forming the distal portion 212 has a flattened rather than round cross section with a flattening height between 0.003" and 0.005". This flattened configuration work hardens any metal that the distal portion 212 may be comprised of and enhances the retention of the flexible distal curve configuration 214. Further, the flattened configuration facilitates greater flexibility of the distal portion 212, enhancing the atraumatic nature of the distal tip 210 when unsupported by a stiff accessory device and reducing the risk of undesired damage to tissue. In some embodiments, the distal length 230 comprises a first distal length section 232 and a second distal length section 234. The second distal length section 234 is partially comprised of the distal tip 210 and is deflected away from the first distal length section 232 and substantially opposite to the distal deflective portion 216. The second distal length section 234 may prevent the distal tip 210 from contacting the wall of a hollow lumen 110 like that shown in FIG. 1 while being slidably inserted therethrough and without substantially kinking or causing damage to the hollow lumen 110 of an elongated introducer assembly 100 like that shown in FIG. 1.

With reference to FIG. 12 to FIG. 19, a series of example workflow steps are shown where an elongated introducer assembly 100 and an elongated guidewire apparatus 200 are used to puncture a first biological wall 910 positioned proximate to a second biological wall 912.

Figure 12:
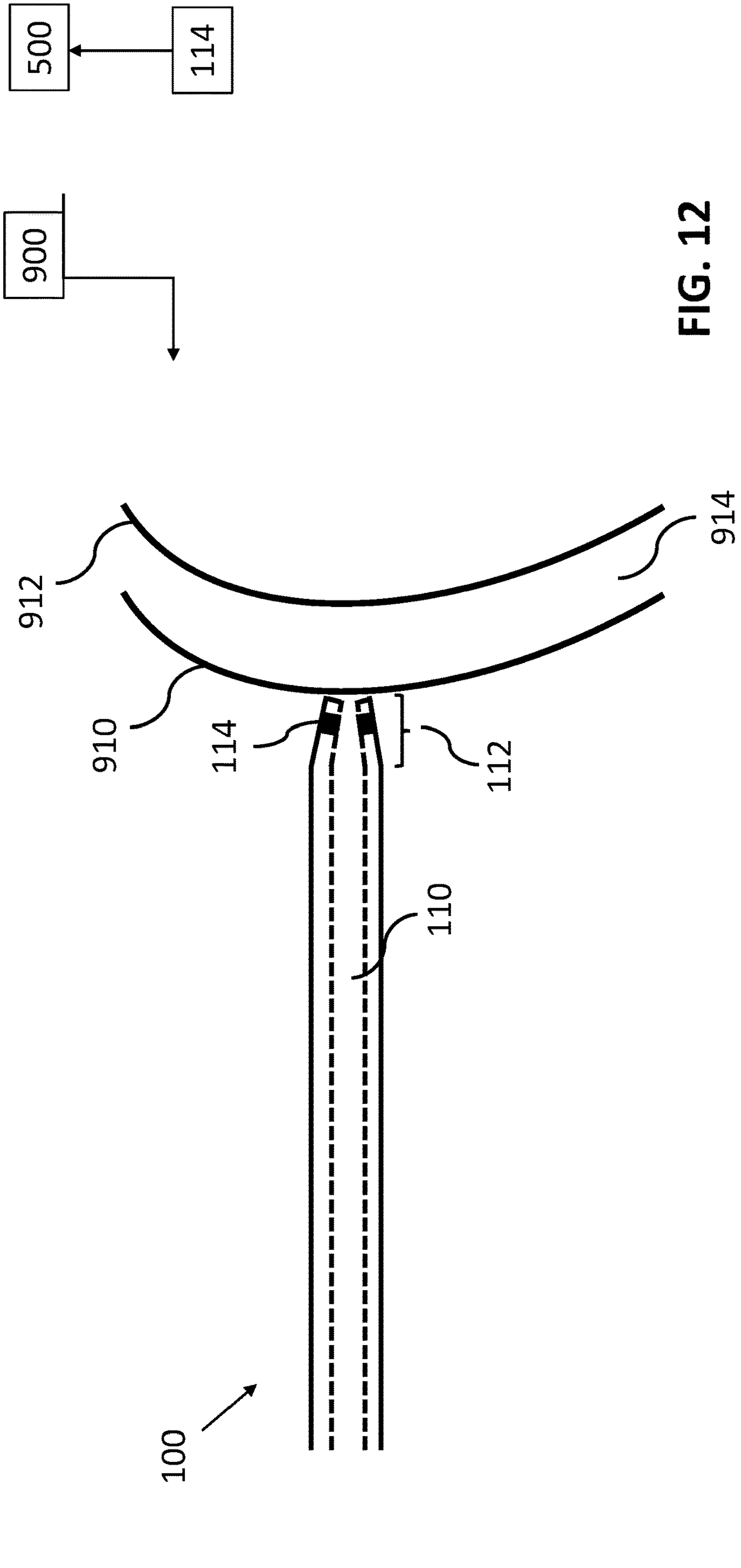
FIG. 12 depicts a cross section view of an elongated introducer assembly positioned proximate to a first biological wall.

With reference to FIG. 12, an elongated introducer assembly 100 is shown inside of a patient 900 and positioned proximate to a first biological wall 910 of the pericardium. Proximate to the first biological wall 910 is a second biological wall 912 of the pericardium. A pericardium space 914 is present between the first biological wall 910 and the second biological wall 912. In this example, the pericardium space 914 is larger than it is typically, due to the presence of a pericardial effusion, where an excess amount of fluid is accumulated in the pericardium space 914 that needs to be drained. A hollow lumen 110 of the elongated introducer assembly slidably receives a compatible accessory device. In some embodiments, the distal section 112 contains an ultrasonically visible marker 114 that is distinguishable on a medical imaging system 500 such as ultrasound, allowing a user to visually identify the distal section 112 when the distal section is inside of the patient 900.

Figure 13:
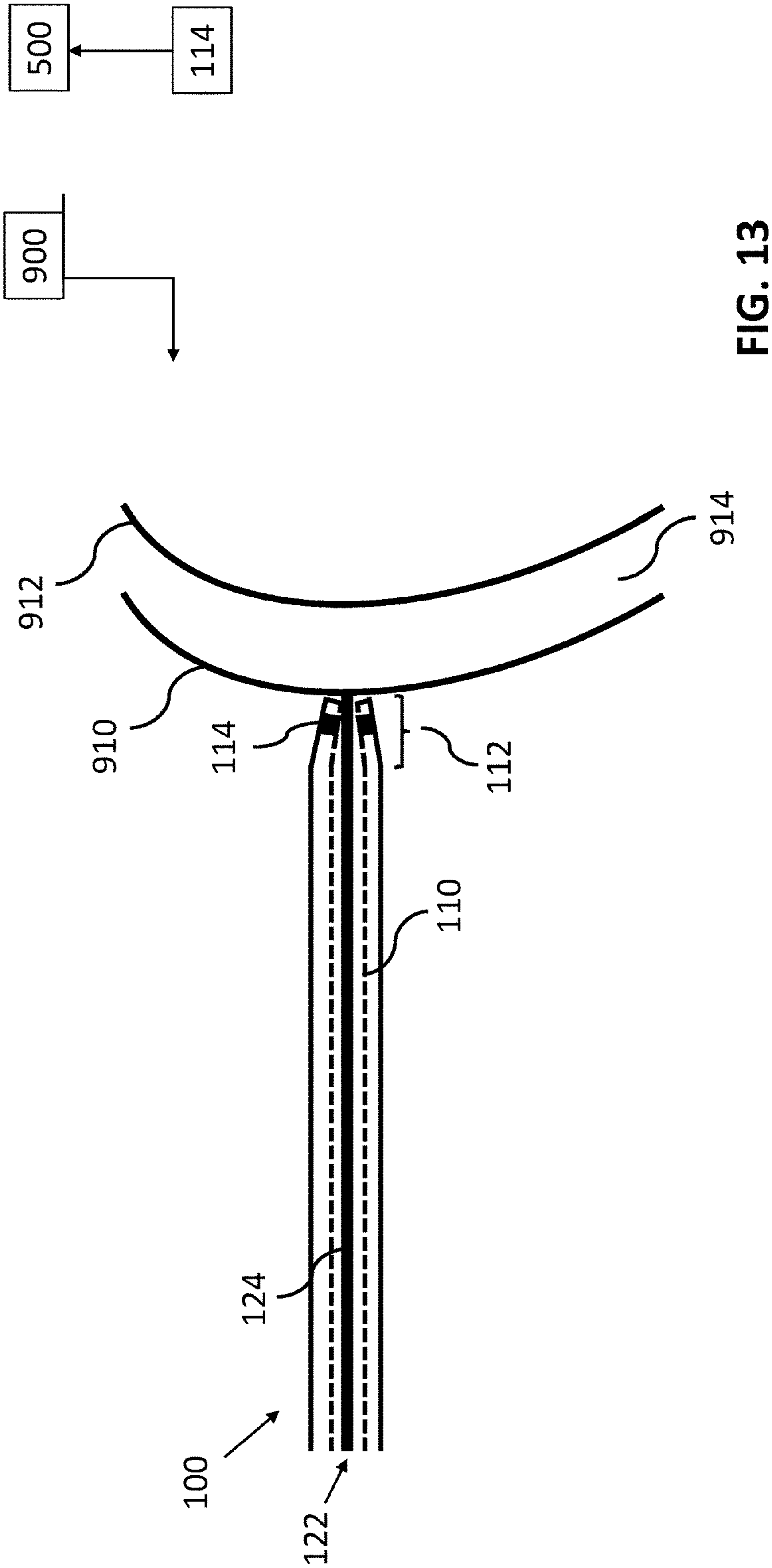
FIG. 13 depicts a cross section view of an elongated introducer assembly with a stylet positioned proximate to a first biological wall.

With reference to FIG. 13, an elongated introducer assembly 100 is shown inside of a patient 900 positioned proximate to a first biological wall 910 where the first biological wall 910 is the outer layer of pericardium (parietal pericardium). Proximate to the first biological wall 910 is a second biological wall 912 where the second biological wall 912 is the inner layer of pericardium (visceral pericardium). A pericardium space 914 is present between the first biological wall 910 and the second biological wall 912. In this example, the pericardium space 914 is larger than is typical due to the presence of a pericardial effusion, where an excess amount of fluid is accumulated in the pericardium space 914 that needs to be drained. A stylet 122 is shown where the stylet shaft 124 occupies a hollow lumen 110. The stylet 122 may add stiffness to the elongated introducer assembly 100, aiding in positioning and advancement towards the first biological wall 910. The stylet 122 may also prevent the buildup of tissue inside of the hollow lumen during insertion of the elongated introducer assembly 100 into the patient. This may help to prevent blockage of the hollow lumen 110 or deposition of tissue inside of the hollow lumen 110 into the pericardium space 914 upon puncture of the first biological wall 910. In some embodiments, a distal section 112 contains an ultrasonically visible marker 114 that is distinguishable on a medical imaging system 500 such as ultrasound, allowing a user to visually identify the distal section 112 when the distal section is inside of the patient 900.

Figure 14:
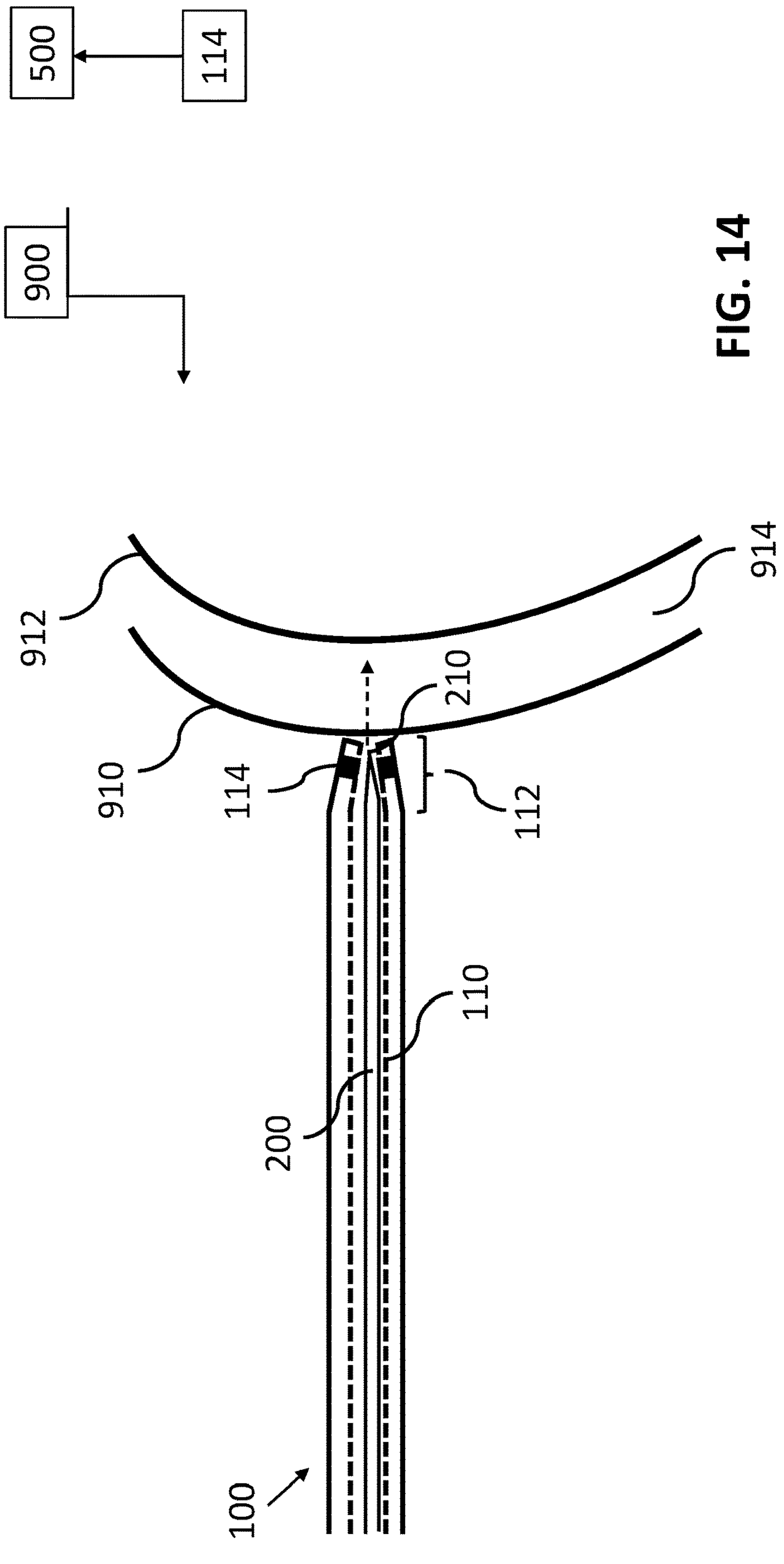
FIG. 14 depicts a cross section view of an elongated introducer assembly with an elongated guidewire assembly contained within the lumen and positioned proximate to a first biological wall.

With reference to FIG. 14, an elongated guidewire assembly 200 is shown occupying a hollow lumen 110 of the elongated introducer assembly 100. The elongated guidewire assembly 200 is selectively maneuvered along the elongated introducer assembly 100 by a user and may be urged towards the first biological wall 910. When contained within the hollow lumen 110, the elongated guidewire assembly 200 generally adopts the internal geometry of the elongated introducer assembly 100. In this way, a distal tip 210 of the guidewire assembly is directed towards the first biological wall 910 when the elongated introducer assembly is appropriately positioned and advanced towards the first biological wall 910 to create a puncture.

Figure 15:
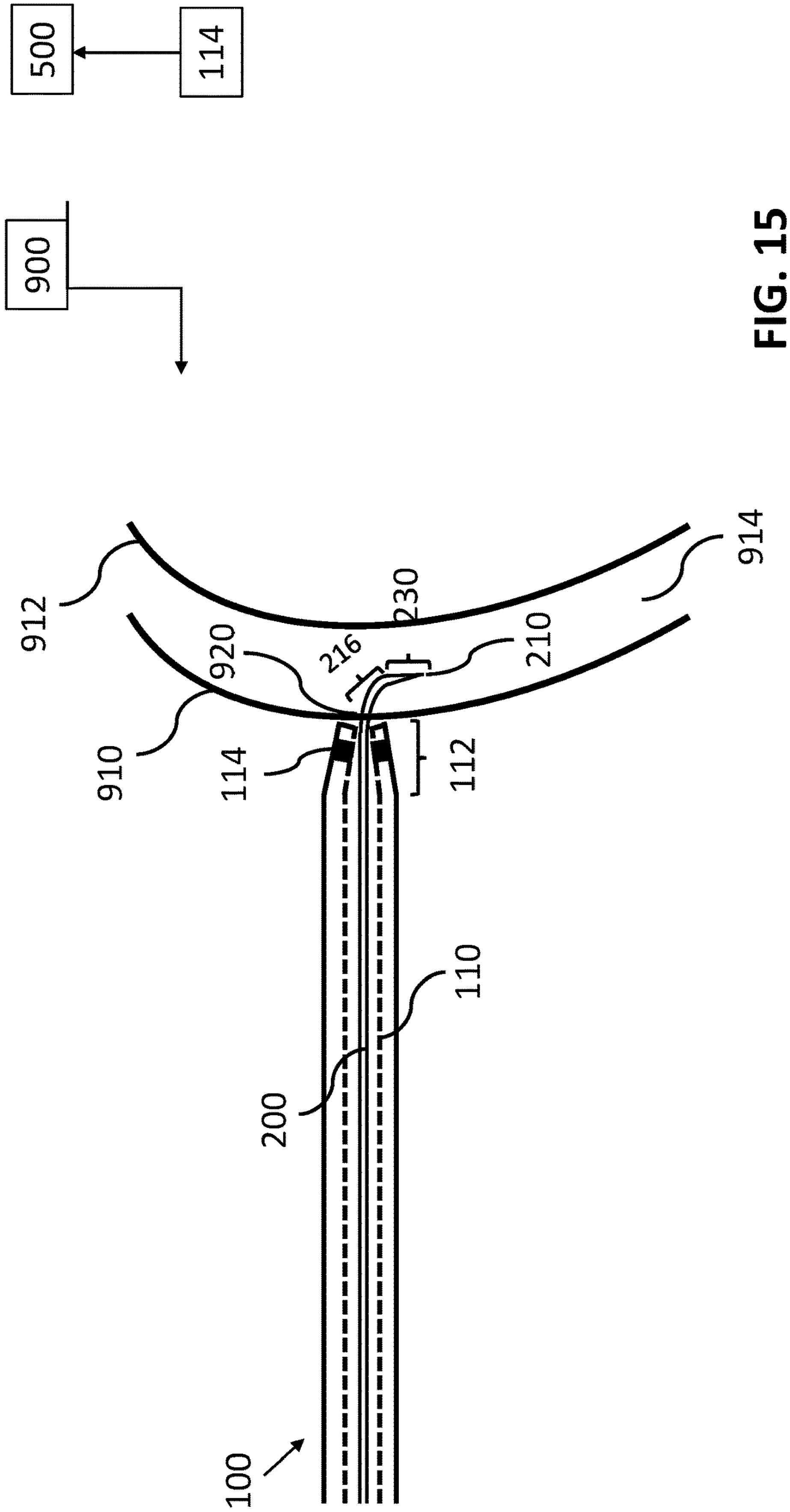
FIG. 15 depicts a cross section view of an elongated introducer assembly with an elongated guidewire assembly puncturing a first biological wall.

With reference to FIG. 15, an elongated introducer assembly 100 is shown inside of a patient 900 positioned proximate to a first biological wall 910. The elongated guidewire assembly 200 is selectively maneuvered along the elongated introducer assembly 100 by a user and urged further into the pericardium space 914. A distal tip 210 is used to create a puncture hole 920 in the first biological wall and a distal deflective portion 216 directs a distal length 230 away from the second biological wall 912 whereby damage or puncture to the second biological wall may be avoided when the elongated guidewire assembly 200 is further urged into the pericardium space 914.

Figure 16:
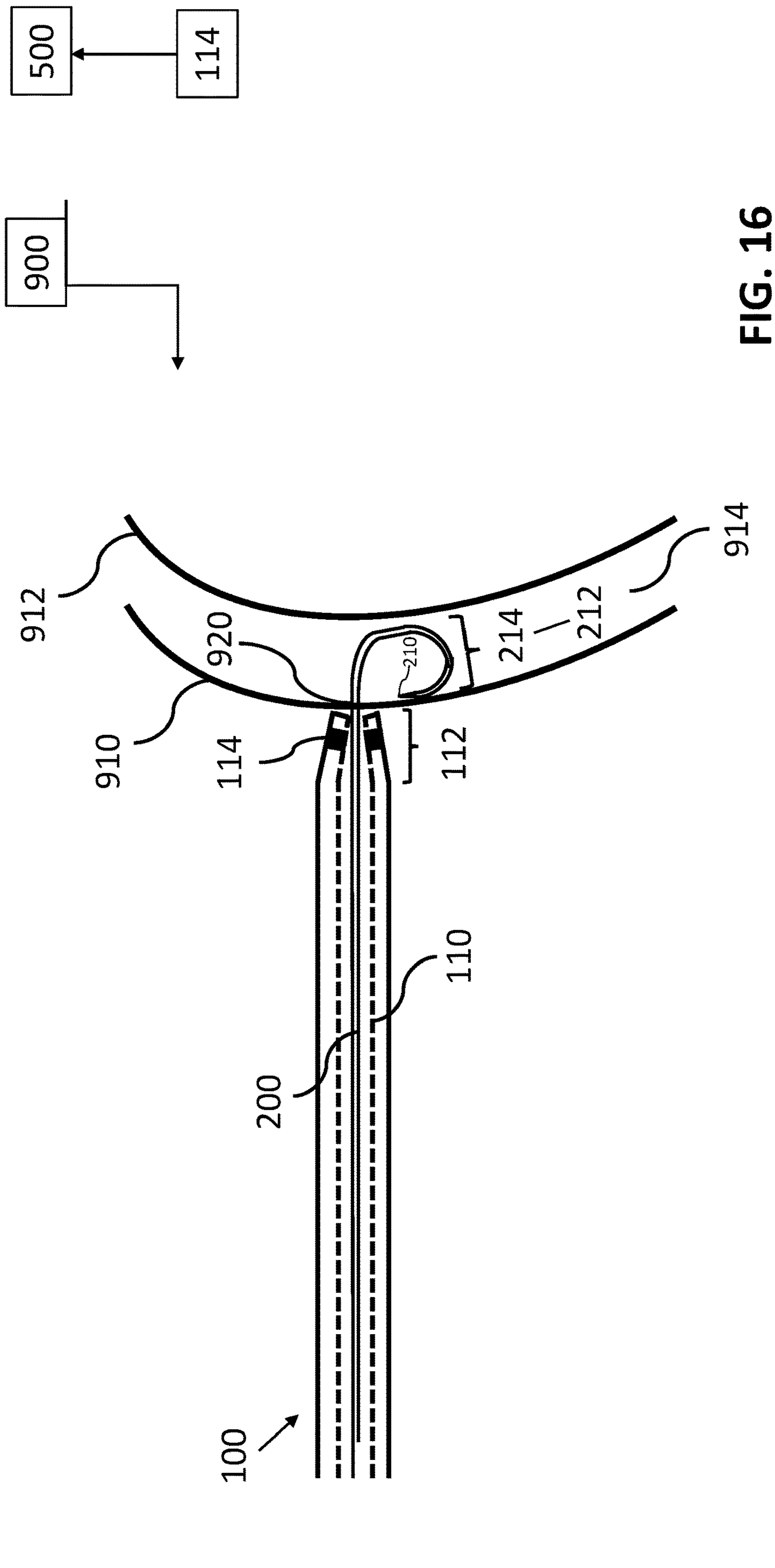
FIG. 16 depicts a cross section view of an elongated introducer assembly with an elongated guidewire assembly inserted through a puncture in a first biological wall.

With reference to FIG. 16, an elongated introducer assembly 100 is shown inside of a patient 900. The elongated guidewire assembly 200 is selectively maneuvered along the elongated introducer assembly 100 by a user. A distal tip 210 is used to create a puncture hole 920 in the first biological wall and upon exit from the elongated introducer assembly 100, a distal portion 212 has a flexible pre-set spatial geometry that adopts a shape that directs the distal tip 210 away from the leading edge of the elongated guidewire assembly 200. In this way, the elongated guidewire assembly 200 may be further advanced into the pericardium space 914 to secure access made by the elongated guidewire assembly 200.

Figure 17:
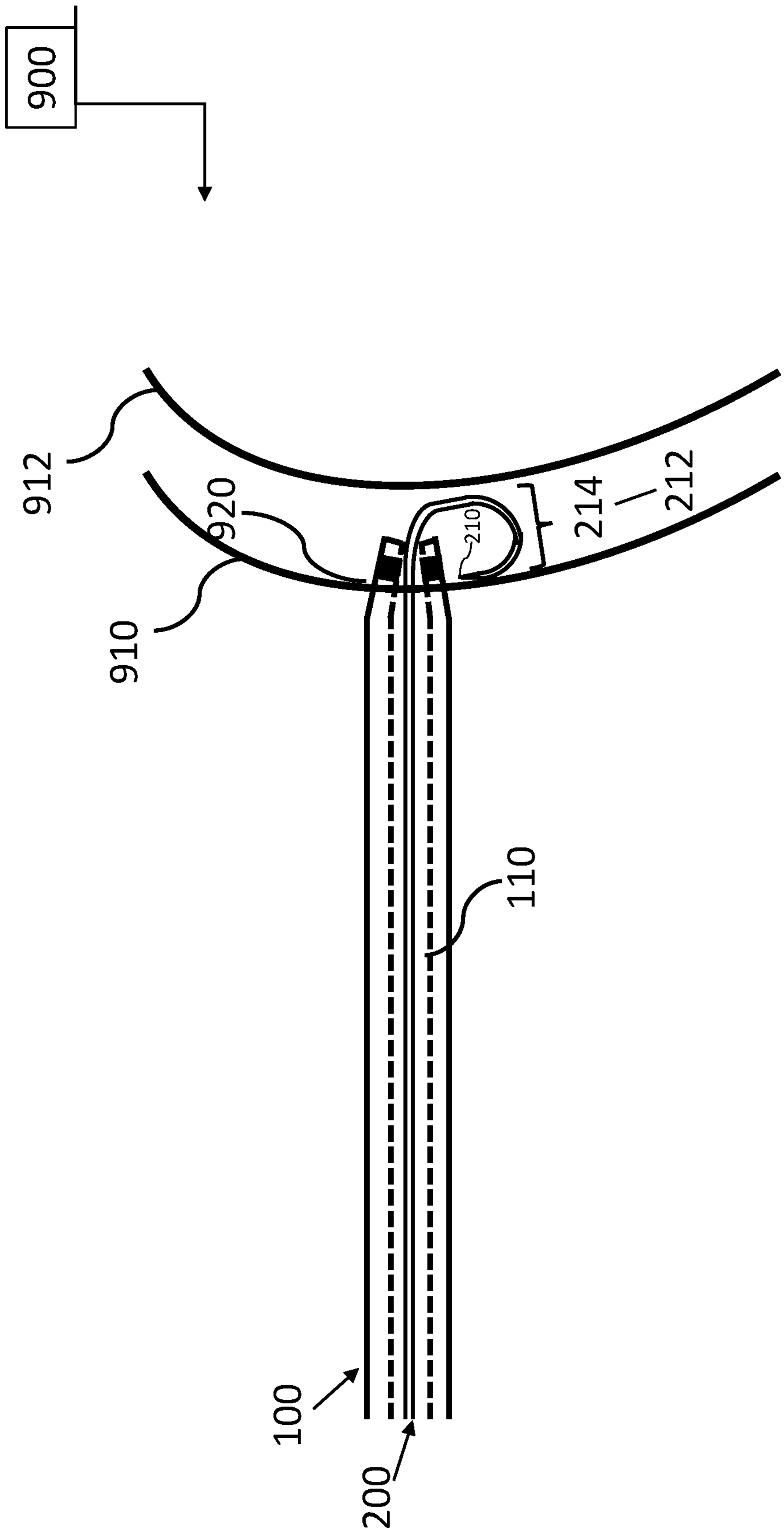
FIG. 17 depicts a cross section view of an elongated introducer assembly dilating a puncture in a first biological wall over an elongated guidewire assembly.

With reference to FIG. 17, an elongated introducer assembly 100 is shown expanding and advancing through a puncture hole 920 made in a first biological wall 910 by a distal tip 210 on an elongated guidewire assembly 200. The elongated guidewire assembly 200 occupies a hollow lumen 110, allowing advancement and retraction of the elongated guidewire assembly 200 and the elongated introducer assembly 100 relative to each other. A distal portion 212 of the elongated guidewire assembly 200 is comprised of a flexible pre-set spatial geometry 214 that directs a distal tip 210 away from the leading edge of the elongated guidewire assembly 200 whereby the elongated guidewire assembly 200 may be further advanced into a pericardium space 914 without, at least in part, puncturing or damaging a second biological wall 912. With the elongated introducer assembly 100 advanced into the pericardium space 914, a user may remove the elongated guidewire assembly 200 from the hollow lumen 110 and drain fluid from the pericardium space 914 through the hollow lumen 110.

Figure 18:
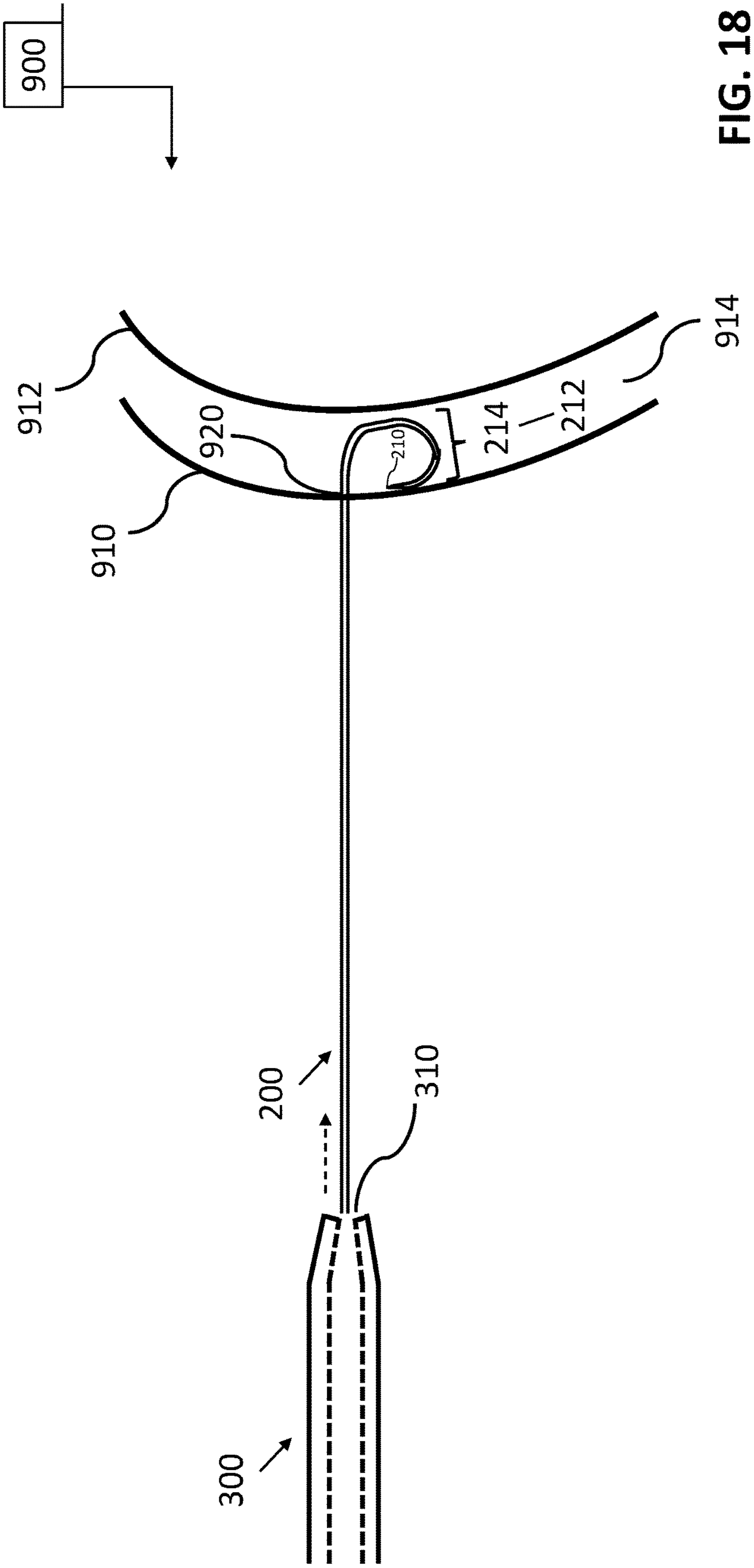
FIG. 18 depicts a cross section view of an elongated catheter apparatus being inserted over an elongated guidewire assembly that is inserted through a puncture in a first biological wall.

With reference to FIG. 18, an embodiment of an elongated guidewire assembly 200 is shown inside of a patient 900 and occupying a pericardium space 914 by traversing a first biological wall 910 through a puncture hole 920 made in the first biological wall 910 via a distal tip 210, where the first biological wall 910 is positioned proximate to a second biological wall 912. The elongated guidewire assembly 200 is depicted here after removal of an elongated introducer assembly 100 from the patient 900 and over the elongated guidewire assembly 200 like that depicted in FIG. 17 following formation of the puncture hole 920. A distal portion 212 of the elongated guidewire assembly 200 is comprised of a flexible preset spatial geometry 214 that directs the distal tip 210 away from the leading edge of the elongated guidewire assembly 200. An elongated catheter apparatus 300 is shown being selectively inserted over the elongated guidewire assembly 200 by insertion through a distal exit portal 310. In this way, the elongated catheter apparatus 300 may be selectively guided over the elongated guidewire assembly 200 towards the first biological wall 910 and the puncture hole 920.

Figure 19:
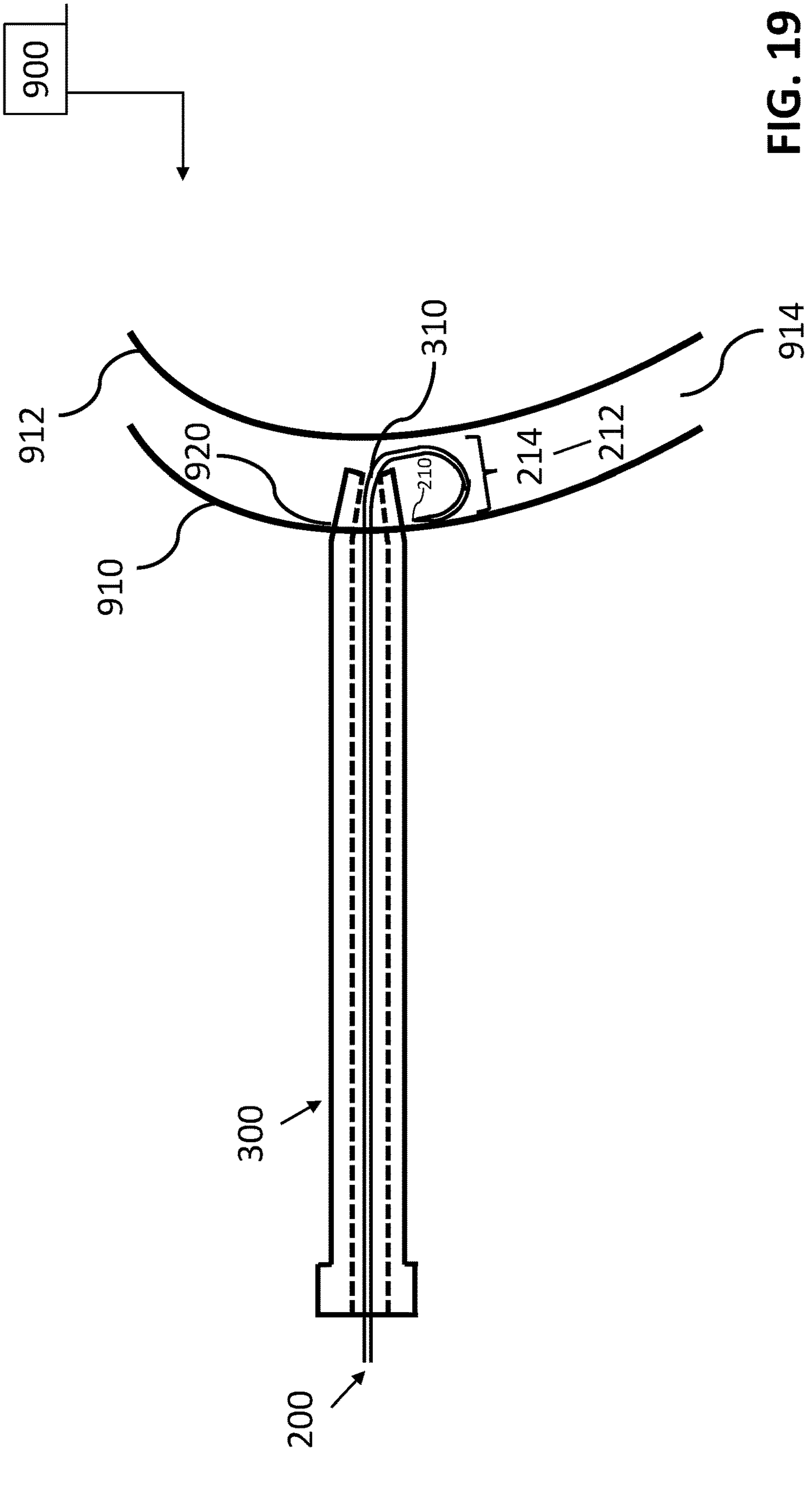
FIG. 19 depicts a cross section view of an elongated catheter apparatus being inserted through a puncture hole in a first biological wall over an elongated guidewire assembly.

With reference to FIG. 19, an elongated catheter apparatus 300 is shown inside of a patient 900 expanding and advancing through a puncture hole 920 in a first biological wall 910 positioned proximate to a second biological wall 912. An elongated guidewire assembly is used to guide the elongated catheter apparatus into a pericardium space 914 through the puncture hole 920. A distal portion 212 of the elongated guidewire assembly 200 is comprised of a flexible preset spatial geometry 214 that directs the distal tip 210 away from the leading edge of the elongated guidewire assembly 200. With the elongated catheter apparatus 300 advanced into the pericardium space 914, a user may remove the elongated guidewire assembly 200 from the elongated catheter apparatus 300 and drain fluid from the pericardium space 914.

The embodiment(s) of the invention described above is(are) intended to be exemplary only. The scope of the invention is therefore intended to be limited solely by the scope of the appended claims.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

We claim:

1. A method for engaging a tissue of a patient having a first biological wall and a second biological wall, the method comprising:

a. advancing an elongated introducer assembly towards the first biological wall within the patient and positioning said elongated introducer assembly proximate to said first biological wall;

b. slidably inserting an elongated guidewire assembly into a hollow lumen of said elongated introducer assembly and urging a distal portion of said elongated guidewire assembly towards said first biological wall;

c. creating a puncture hole in said first biological wall with a distal tip located on said elongated guidewire assembly; and d. deflecting a distal length that comprises said distal tip away from said second biological wall via a distal deflective portion positioned a minimum of 4 mm away from said distal tip;

e. removing said elongated introducer assembly from said patient while said elongated guidewire assembly remains in position traversing said first biological wall through said puncture hole; and f. slidably receiving the elongated guidewire assembly via a distal exit portal of an elongated catheter apparatus, wherein said elongated guidewire assembly is used to guide said elongated catheter apparatus into said patient and across said first biological wall.

2. The method of claim 1, wherein said puncture hole is expanded by said elongated introducer assembly.

3. The method of claim 1, wherein said elongated introducer assembly further comprises a stylet that is slidably received by said hollow lumen of said elongated introducer assembly.

4. The method of claim 1, wherein a hemostasis valve is attached to a proximal hub of said elongated introducer assembly and fluid is injected or aspirated at any step.

5. The method of claim 1, wherein the elongated introducer assembly includes an ultrasonically visible marker positioned at a distal section of the elongated introducer assembly, and wherein the method further comprises monitoring a position of said distal section within the patient using a medical imaging system during the advancing step.

6. The method of claim 1, wherein the elongated guidewire assembly comprises a detectable marker, and wherein the method further comprises monitoring a position of the elongated guidewire assembly within the patient using a medical imaging system during the creating and deflecting steps.

7. The method of claim 1, wherein the distal portion of the elongated guidewire assembly comprises an elastic material selected from nitinol and stainless steel, and wherein said distal portion adopts a straightened state when inside the hollow lumen of the elongated introducer assembly and returns to a preset spatial geometry upon exiting said elongated introducer assembly.

8. The method of claim 1, wherein the distal tip has a width no greater than 0.001 inch.

9. The method of claim 1, wherein the distal portion is in a flattened configuration with a height between 0.003 inches and 0.005 inches.

10. The method of claim 1, wherein the distal length comprises a first distal length section and a second distal length section, wherein said second distal length section contains the distal tip and is deflected from the first distal length section in a direction generally opposite to the distal deflective portion.

11. The method of claim 1, wherein the elongated introducer assembly has a proximal hub comprising a female luer connector, and wherein the method further comprises connecting a luer-compatible accessory to said female luer connector during the procedure.

12. The method of claim 1, further comprising, after creating the puncture hole in the first biological wall with the distal tip, further advancing the elongated guidewire assembly into the pericardial space defined between the first biological wall and the second biological wall to secure access through the first biological wall.

13. The method of claim 2, further comprising, after expanding the puncture hole in the first biological wall by advancing the elongated introducer assembly therethrough, removing the elongated guidewire assembly from the hollow lumen of the elongated introducer assembly and draining fluid from the pericardial space through the hollow lumen of the elongated introducer assembly.

* * * * *